United States Patent [19]

Arrowsmith et al.

[11] Patent Number: 5,006,561
[45] Date of Patent: Apr. 9, 1991

[54] INDANE SULFONAMIDE ANTI-ARRHYTHMIC AGENTS AND USE

[75] Inventors: John E. Arrowsmith, Upper Walmer; Peter E. Cross, Canterbury, both of England

[73] Assignee: Pfizer Inc., New York, N.Y.

[21] Appl. No.: 510,370

[22] Filed: Apr. 17, 1990

Related U.S. Application Data

[63] Continuation of Ser. No. 164,310, Mar. 4, 1988, abandoned.

[30] Foreign Application Priority Data

Mar. 25, 1987 [GB] United Kingdom ............... 870123

[51] Int. Cl.$^5$ ............... A61K 31/18; C07C 311/08
[52] U.S. Cl. ............... 514/605; 564/82; 564/354; 564/374; 564/384
[58] Field of Search ............... 564/83, 99, 353, 82; 514/605, 821

[56] References Cited

U.S. PATENT DOCUMENTS 4,959,500  9/1990  Schleifstein ............... 564/82

FOREIGN PATENT DOCUMENTS 1518652  4/1969  Fed. Rep. of Germany.

Primary Examiner—Richard L. Raymond
Attorney, Agent, or Firm—Peter C. Richardson; Paul H. Ginsburg

[57] ABSTRACT

Novel 5-alkanesulphonamido-2-[N-(4-alkanesulphonamidophenoxyalkyl)-N-methylamino]indane and 5-alkanesulphonamido-2-[N-(4-alkanesulphonamidophenyl-alkyl)-N-methylamino]indane compounds have been prepared, including their pharmaceutically acceptable salts and various key novel intermediates therefor. These compounds are useful in therapy as anti-arrhythmic agents and therefore, are of value in the treatment of various cardiac arrhythmias. The most preferred member compouned is 5-methanesulphonamido-2-[N-(4-methanesulphonamidophenethyl)-N-methylamino]indane. Methods for preparing these compounds from known starting materials are provided.

9 Claims, No Drawings

INDANE SULFONAMIDE ANTI-ARRHYTHMIC AGENTS AND USE

This is a continuation, of application Ser. No. 07/164,310, filed on Mar. 4, 1988, and now abandon.

BACKGROUND OF THE INVENTION

This invention relates to certain indane sulfonamides which are antiarrhythmic agents, and to intermediates therefor.

The antiarrhythmic agents of the invention prolong the duration of the action potential in cardiac muscle and conducting tissue, and thereby increase refractoriness to premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

SUMMARY OF THE INVENTION

Thus the invention provides compounds of the formula:

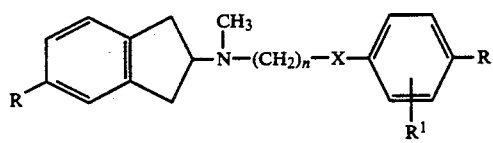

and their salts, wherein
each R, which is the same, is $-NO_2$, $-NH_2$ or $-NHSO_2(C_1-C_4\ alkyl)$;
X is O or a direct link;
$R^1$ is H, $C_1-C_4$ alkyl, $C_1-C_4$ alkoxy or halo; and
n is 1 or 2, with the proviso that when X is O, n is 2.

The compounds of the formula (A) in which each R is $-NHSO_2(C_1-C_4\ alkyl)$ are antiarrhythmic agents. The compounds of the formula (A) in which each R is $-NO_2$, or each R is $-NH_2$, are synthetic intermediates.

Thus the invention provides antiarrhythmic agents of the formula:

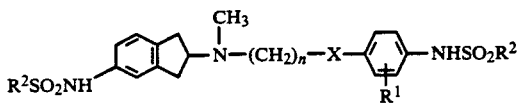

and their pharmaceutically acceptable salts, wherein
$R^1$ is H, $C_1-C_4$ alkyl, $C_1-C_4$ alkoxy or halo;
each $R^2$, which is the same, is $C_1-C_4$ alkyl;
X is O or a direct link; and
n is 1 or 2, with the proviso that when X is O, n is 2.

The preferred alkyl group is methyl. The preferred alkoxy group is methoxy. $C_3$ and $C_4$ alkyl and alkoxy groups can be straight or branched chain. "Halo" means F, Cl, Br, or I.

$R^1$ is preferably H.

The preferred antiarrhythmic agent of the formula (I) has the structure:

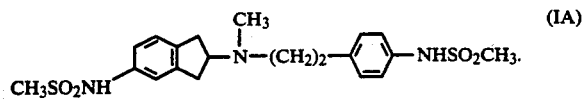

The compounds of the formula (A) are optically active and thus the invention includes the R, S and R/S forms.

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. Also included are the alkali metal salts, particularly the sodium and potassium salts. The salts are preparable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the formula (I) will be in the range from 2 to 150 mg. daily, taken in and up to 4 divided doses per day, for an average adult patient (70 kg). Dosages for intravenous administration would be expected to be within the range 1.0 to 20 mg per single dose as required. A severe cardiac arrythmia is preferably treated by the i.v. route in order to effect a rapid conversion to the normal rhythm. Thus for a typical adult patient individual tablets or capsules might contain 2 to 50 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament, particularly for use as an antiarrhythmic agent.

The invention also provides the use of a compound of the formula (I), or of a pharmaceutically acceptable salt thereof, for the manufacture of a medicament for the prevention or reduction of cardiac arrhythmias.

DETAILED DESCRIPTION OF THE INVENTION

The compounds of the formula (I) can be prepared by the acylation of compounds of the formula (A) in which each R is —$NH_2$, using a $C_1$-$C_4$ alkanesulphonyl chloride or bromide, or a $C_1$-$C_4$ alkanesulphonic anhydride. Clearly at least two equivalents of the acylating agent will be required and, of course, the R groups in the final product will be the same.

The reaction is typically carried out at room temperature, and optionally in the presence of an acid acceptor such as pyridine, triethylamine, potassium carbonate or sodium bicarbonate. The presence of an acid acceptor is particularly useful when an alkanesulphonyl chloride or bromide is used. It is in fact particularly convenient to carry out the reaction using an alkanesulphonyl chloride in pyridine which functions both as the acid acceptor and as the solvent. The product of the formula (I) can then be isolated and purified by conventional means.

The starting materials of the formula (A) in which each R is —$NH_2$ can be prepared by the reduction of the corresponding compounds in which each R is —$NO_2$ according to conventional techniques, e.g. by using $H_2$/Pd/C in a suitable organic solvent, e.g. ethyl acetate or a mixture of ethyl acetate and methanol, at about room temperature.

The starting materials of the formula (A) in which each R —$NO_2$ can be prepared as follows:

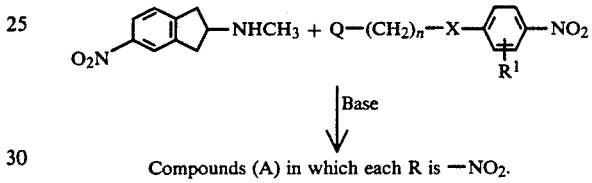

Compounds (A) in which each R is —$NO_2$.

Q is a leaving group such as Cl, Br, I, methanesulphonyloxy, benzenesulphonyloxy or toluenesulphonyloxy. Q is preferably Br. The reaction is typically carried out in an organic solvent, e.g. acetonitrile or acetonitrile/ethanol, under reflux and in the presence of a base such as potassium carbonate or sodium bicarbonate.

The indane starting material can be prepared by the procedure illustrated in detail in Preparations 1 to 3. The substituted nitrobenzene starting materials are in general known compounds or can be prepared analogously to the methods of the prior art such as those described in the following Preparations.

When n is 1 or 2 and X is a direct link, then the following routes, which are illustrated in detail in the following Preparations, can also be used to prepare the starting materials of the formula (A) in which each R is —$NO_2$:

(a) [n = 2]

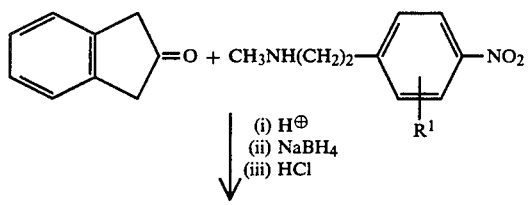

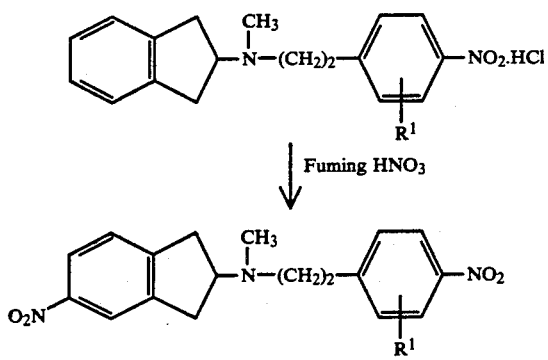

and

<u>(b) [n = 1]</u>

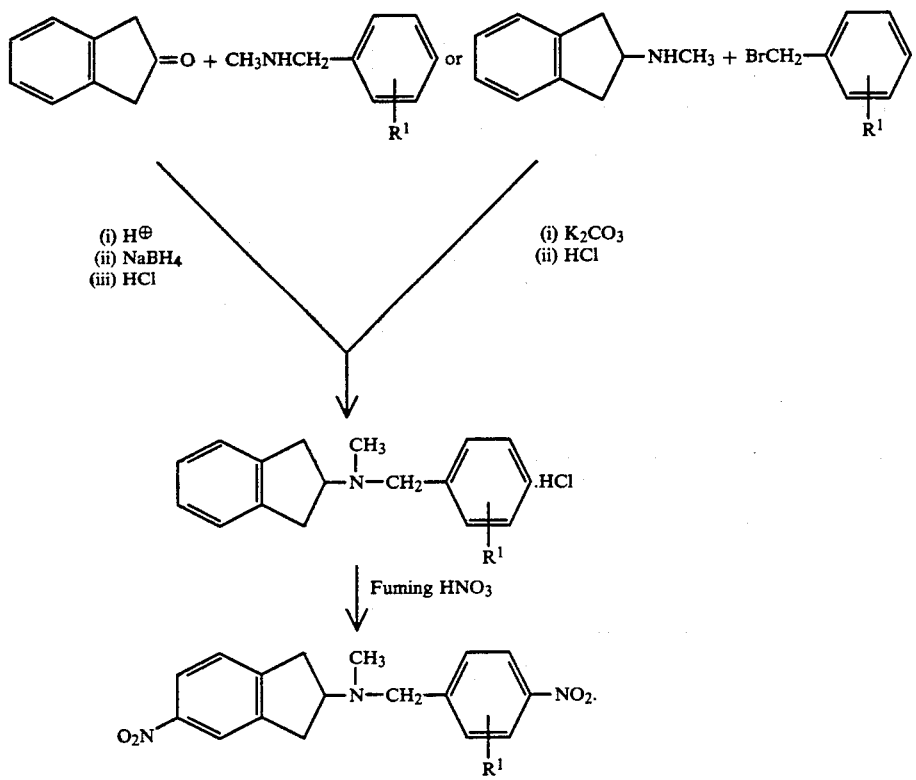

The following Examples, in which all temperatures are in ° C., illustrate the preparation of the compounds of the formula (I):

EXAMPLE 1

5-Methanesulphonamido-2-[N-(2-{4-methanesulphonamidophenoxy}ethyl)-N-methylamino]indane

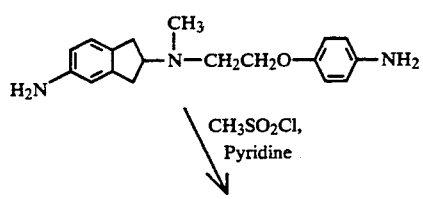

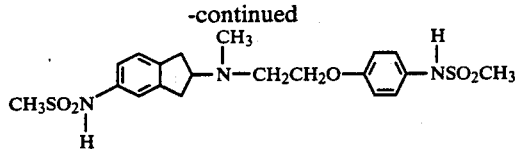

Methanesulphonyl chloride (0.15 ml) was added to a solution of 5-amino-2-[N-(2-{4-aminiophenoxy}ethyl)-N-methylamino]indane (0.25 g) in pyridine and the reaction mixture was stirred at room temperature for 17 hours. The solvent was then removed by evaporation in vacuo to give a gum which was purified by column chromatography on silica eluting with methylene chloride containing methanol (0% up to 1%). The product-containing fractions were combined and evaporated in vacuo to give the title compound as a foam, yield (0.06 g).

¹H-N.m.r. (CDCl₃): δ=7.25 (d, 2H); 7.2 (d, 1H); 7.1 (s, 1H); 7.0 (d, 1H); 6.95 (d, 2H); 4.1 (t, 2H); 3.55 (t, 1H); 3.1 (m, 2H); 3.05 (s, 3H); 3.0 (s, 3H); 2.9 (m, 4H); 2.45 (s, 3H).

EXAMPLE 2

5-Methanesulphonamido-2-[N-(4-methanesulphonamidophenethyl)-N-methylamino]indane

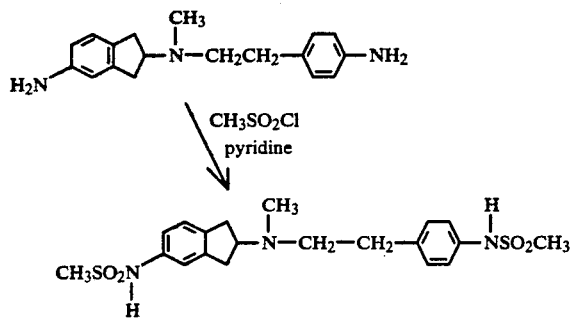

Methanesulphonyl chloride (0.155 ml) was added to a solution of 5-amino-2-[N-(4-aminophenethyl)-N-methylamino]indane (0.28 g) in pyridine (30 ml) and the reaction mixture was stirred at room temperature for 17 hours. The solvent was then removed by evaporation in vacuo to give a gum which was dissolved in methylene chloride, washed with aqueous sodium bicarbonate and brine, dried (MgSO₄) and evaporated in vacuo. The residue was purified by column chromatography on silica eluting with methylene chloride containing methanol (0% up to 2%) and the product-containing fractions were combined and evaporated to dryness in vacuo to afford the title compound as a foam, yield 0.27 g.

Analysis %: Found: C,54.5; H,6.2; N,9.35; Calculated for C₂₀H₂₇N₃O₄S₂: C,54.9; H,6.2; N,9.6.

¹H-N.m.r. (CDCl₃): δ=7.2 (q, 4H); 7.15 (d, 1H); 7.1 (s, 1H); 7.0 (d, 1H); 3.45 (t, 1H); 3.05 (m, 2H); 3.0 (d, 6H); 2.95 (m, 2H); 2.90 (m, 2H); 2.85 (m, 2H); 2.4 (s, 3H).

EXAMPLE 3

5-Methanesulphonamido-2-[N-(4-methanesulphonamidobenzyl)-N-methylamino]indane

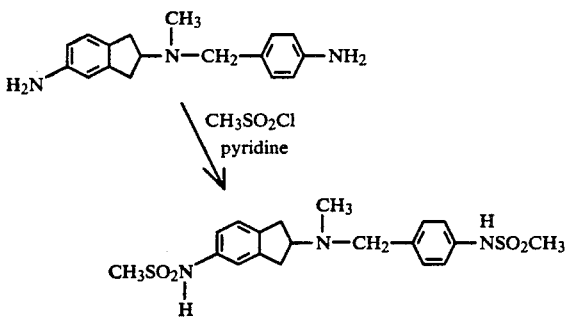

Methanesulphonyl chloride (0.53 ml) was added to 5-amino-2-[N-(4-aminobenzyl)-N-methylamino]indane (1.1 g) in pyridine and the reaction mixture was stirred at room temperature for 17 hours. The solvent was then removed by evaportion in vacuo and the residue taken up in methylene chloride, washed with aqueous sodium bicarbonate, dried (MgSO₄) and evaporated in vacuo. The resulting gum was purified by column chromatography on silica eluting with methylene chloride containing methanol (0% up to 2%). The product-containing fractions were combined and evaporated to dryness in vacuo to give the title compound as a colourless foam. This foam was dissolved in chloroform and the solution was evaporated to dryness in vacuo to give the title compound as a colourless foam, yield 0.2 g.

Analysis %: Found: C,54.0; H,6.0; N,9.5; Calculated for C₁₉H₂₅N₃O₄.2/3 CHCl₃*: C,53.9; H,5.9; N,9.6.

* The fact that the product was solvate was detected and quantified by ¹H-n.m.r.

¹H-N.m.r. (TFAd): δ=7.72 (s, 1H); 7.63 (t, 1H); 7.45 (d, 2H); 7.4 (t, 2H); 7.3 (s, 1H); 4.8 (d, 1H); 4.5 (m, 1H); 4.35 (d, 1H); 3.6 (m, 4H); 3.2 (d, 6H); 2.9 (d, 3H).

The following Preparations, in which all temperatures are in ° C., illustrate the preparation of the starting materials used in the Examples:

PREPARATION 1

2-Formylaminoindane

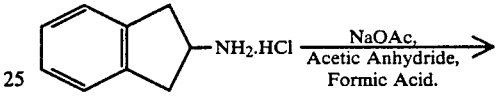

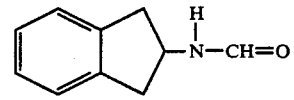

Acetic anhydride (40 ml) and formic acid (20 ml) were mixed and heated at 50° for 15 minutes with stirring. 2-Aminoindane hydrochloride (25 g) (see J. Med. Chem., 1980, 23, page 745) and sodium acetate (20 g) were added to this mixture which was then stirred at room temperature for 24 hours. The reaction mixture was poured into ice/water and extracted three times with methylene chloride. The combined organic layers were washed with water and aqueous sodium carbonate, dried (MgSO₄) and evaporated in vacuo to give the title compound, yield 17.6 g, m.p. 72°–74°.

Analysis %: Found: C,74.25; H,7.0; N,8.6; Calculated for C₁₀H₁₁NO: C,74.5; H,6.9; N,8.7.

¹H-N.m.r. (CDCl₃): δ=8.0 (s, 1H); 7.1 (s, 4H); 4.7 (m, 1H); 3.4 (dd, 2H); 2.8 (dd, 2H).

PREPARATION 2

2-Formylamino-5-nitroindane

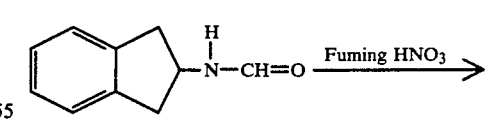

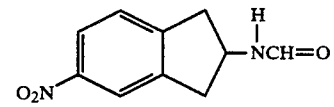

2-Formylaminoindane (15 g) was added portionwise to fuming nitric acid (30 ml, density=1.5 g/ml) whilst keeping the temperature at between 0° and −5°. Stirring was continued for 1 hour at 0° before pouring the reaction mixture onto ice/water and extracting with methylene chloride. The organic layer was washed with aqueous sodium bicarbonate, dried (MgSO₄) and evaporated in vacuo to give an oil which was purified by column chromatography on silica eluting with methylene chloride containing hexane (20% down to 0%) and then methylene chloride containing methanol (0% up to 2%). The product-containing fractions were combined and evaporated to give the title compound, yield 7.7 g, m.p. 91°-92°.

Analysis %: Found: C,58.1; H,4.8; N,13.5; Calculated for $C_{10}H_{10}N_2O_3$: C,58.25; H,4.9; N,13.6.

PREPARATION 3

2-Methylamino-5-nitroindane hydrochloride

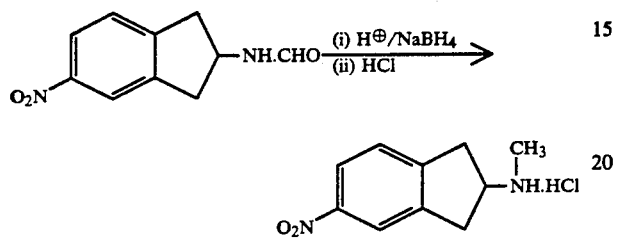

Acetic acid (6.4 ml) was added dropwise to a stirred mixture of 2-formylamino-5-nitroindane (4.6 g) and sodium borohydride (4.22 g) in tetrahydrofuran (65 ml) cooled to 0°-5°. Stirring was continued at 0°-5° for 15 minutes before heating the reaction mixture at reflux for 2 hours. The reaction mixture was then evaporated to dryness in vacuo and the residue was diluted with 2M hydrochloric acid, then made basic (to a pH of about 12) with aqueous sodium carbonate and extracted with methylene chloride. The organic layer was dried (MgSO₄), evaporated in vacuo and the residue stirred with ethereal hydrogen chloride to afford a precipitate which was filtered and dried to give the title compound, yield 1.5 g, m.p. 221°-223°.

Analysis %: Found: C,52.75; H,5.6; N,12.15; Calculated for $C_{10}H_{12}N_2O_2 \cdot HCl$: C,52.5; H,5.7; N,12.25.

PREPARATION 4

2-[N-Methyl-N-(2-{4-nitrophenoxy}ethyl)amino]-5-nitroindane

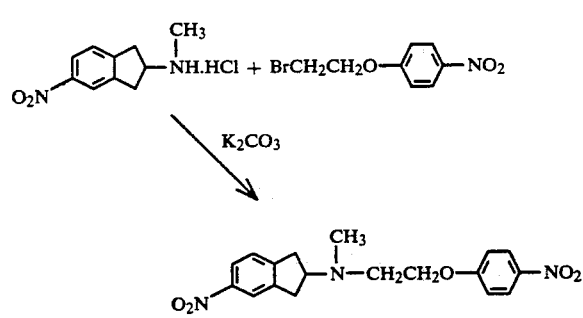

2-Methylamino-5-nitroindane hydrochloride (0.46 g), 2-bromoethoxy-4-nitrobenzene (0.49 g) [see C.A., (1960), 54, 11046a] and potassium carbonate (2 g) were heated under reflux in acetonitrile (50 ml)/ethanol (20 ml) for 20 hours. The solvent was then removed by evaporation in vacuo and the residue diluted with water and extracted with methylene chloride. The organic layer was dried (MgSO₄) and evaporated to give an oil which was purified by column chromatography on silica eluting with methylene chloride containing methanol (0% up to 1%). The product-containing fractions were combined and evaporated to give the title compound as an oil, yield 0.28 g.

'H-N.m.r. (CDCl₃): δ=8.0 (d, 2H); 7.9 (m, 2H); 7.2 (d, 1H); 6.8 (d, 2H); 4.1 (t, 2H); 3.4 (m, 1H); 2.9 (br d, 4H); 2.8 (t, 2H); 2.3 (s, 3H).

PREPARATION 5

5-Amino-2-[N-(2-{4-aminophenoxy}ethyl)-N-methylamino]indane

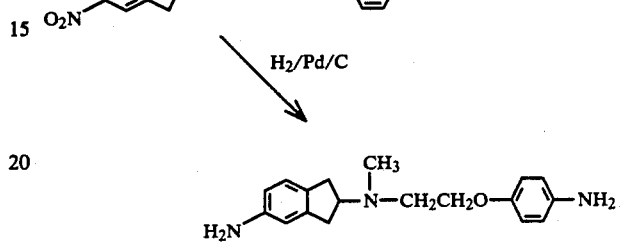

A solution of 2-[N-methyl-N-(2-{4-nitrophenoxy}ethyl)amino]-5-nitroindane (0.3 g) in ethyl acetate (30 ml) containing 5% Pd/C (0.03 g) was stirred under a hydrogen atmosphere [206.8 kPa (30 p.s.i.)] for 2 hours at room temperature. The catalyst was then removed by filtration and the filtrate evaporated in vacuo to afford the title compound as a gum, yield 0.25 g, which was used directly without further purification.

PREPARATION 6

2-[N-Methyl-N-(4-nitrophenethyl)amino]-5-nitroindane

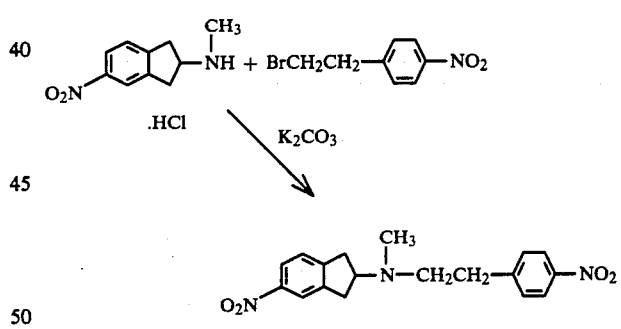

2-Methylamino-5-nitroindane hydrochloride (0.45 g), 4-nitrophenethyl bromide (0.46 g) and potassium carbonate (2 g) were heated under reflux in acetonitrile (30 ml) for 3 days. The reaction mixture was then filtered, the filtrate evaporated in vacuo, and the residue purified by column chromatography on silica eluting with methylene chloride containing methanol (0% up to 1%). The product-containing fractions were combined and evaporated in vacuo to give a gum which was crystallised from ethanol affording the title compound, yield 0.16 g, m.p. 138°-141°.

Analysis %: Found: C,62.8; H,5.5, N,12.1; Calculated for $C_{18}H_{19}N_3O_4$: C,63.3; H,5.6; N,12.3.

'H-N.m.r. (CDCl₃): δ=8.2 (d, 2H); 8.1 (d, 1H); 8.05 (s, 1H); 7.4 (d, 2H); 7.3 (d, 1H); 3.5 (t, 1H); 3.15 (q, 2H); 2.9 (m, 4H); 2.8 (t, 2H); 2.4 (s, 3H).

PREPARATION 7

2-[N-Methyl-N-(4-nitrophenethyl)amino]indane hydrochloride

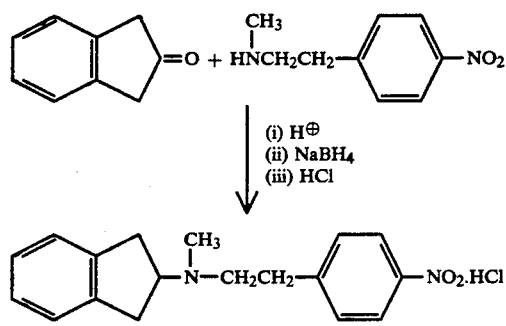

2-Indanone (2.8 g), N-methyl-4-nitrophenethylamine (3.83 g) [see J.O.C., (1956), 21, 45] and toluene-4-sulphonic acid (0.1 g) in toluene (100 ml) were heated under reflux in a Dean and Stark apparatus for 1 hour by which time all the water produced (approximately 0.4 ml) had been collected by azeotroping. The solvent was then evaporated in vacuo and the residue dissolved in ethanol (100 ml) to which was added sodium borohydride (0.8 g) and the mixture was stirred at room temperature for 6 hours. The mixture was then heated at reflux temperature for 10 minutes, cooled and evaporated to dryness in vacuo. The residue was added to 2M hydrochloric acid (150 ml) with stirring, and after a ½ hour, a semi-solid precipitate was filtered off and the filtrate washed with ether and dried to give the title compound, yield 1.2 g, m.p. 201°–203°.

Analysis %: Found: C,64.95; H,6.4; N,8.4; Calculated for $C_{18}H_{20}N_2O_2 \cdot HCl$: C,64.85; H,6.45; N,8.3.

$^1$H-N.m.r. (DMSO d$_6$): δ=8.3 (d, 2H); 7.6 (d, 2H); 7.2 (q, 4H); 4.2 (quintet, 1H); 3.4 (m, 8H); 2.8 (d, 3H).

PREPARATION 8 (ALTERNATIVE TO PREPARATION 6)

2-[N-Methyl-N-(4-nitrophenethyl)amino]-5-nitroindane

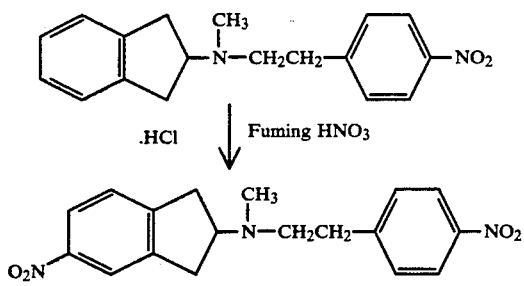

2-[N-Methyl-N-(4-nitrophenethyl)amino]indane hydrochloride (1.2 g) was added portionwise over 10 minutes to fuming nitric acid (20 ml, density=1.5 g/ml) cooled to −5°. Stirring was continued for a further 2 minutes before the reaction mixture was poured into ice/water. The water-containing mixture was extracted with methylene chloride and the organic extract was washed with aqueous sodium bicarbonate, dried (MgSO$_4$) and evaporated to dryness in vacuo. The residue was rectystallised from ethanol to give the title compound, yield 0.78 g, m.p. 138°–140°.

PREPARATION 9

5-Amino-2-[N-(4-aminophenethyl)-N-methylamino]indane

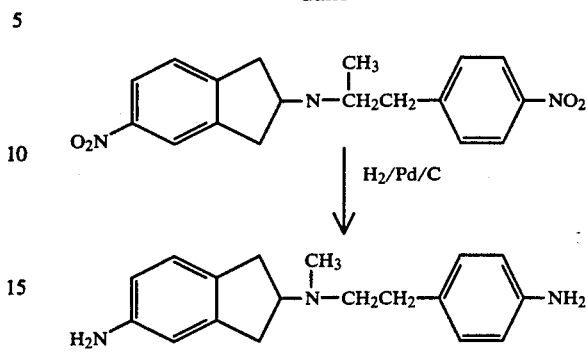

A solution of 2-[N-methyl-N-(4-nitrophenethyl)amino]-5-nitroindane (0.5 g) in ethyl acetate/methanol (40 ml/10 ml) containing 5% Pd/C (0.05 g) was stirred under a hydrogen atmosphere [206.8 kPa (30 psi)] for 4 hours at room temperature. The catalyst was then removed by filtration and the filtrate evaporated in vacuo to give a gum which was triturated with ether. The ether was decanted and evaporated to dryness in vacuo to give the title compound, yield 0.33 g. A small sample was taken and recrystallised from diisopropyl ether, m.p. 112°–114°.

Analysis %: Found: C,76.6; H,8.3; N,14.6; Calculated for $C_{18}H_{23}N_3$: C,76.8; H,8.2; N,14.9.

$^1$H-N.m.r. (CDCl$_3$): δ=7.05 (d, 2H); 7.0 (d, 1H); 6.7 (d, 2H); 6.55 (s, 1H); 6.5 (d, 1H); 3.6 (br s, 4H); 3.4 (quintet, 1H); 3.0 (m, 2H); 2.8 (m, 2H); 2.7 (d, 4H); 2.4 (s, 3H).

PREPARATION 10

2-(N-Benzyl-N-methylamino)indane hydrochloride

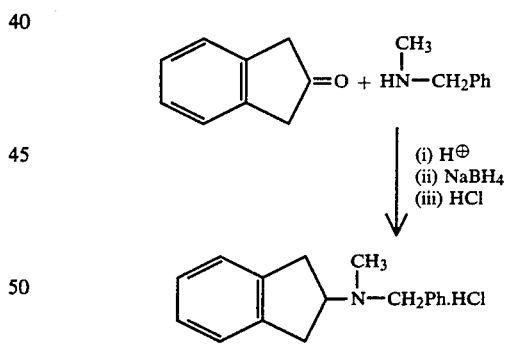

A solution of 2-indanone (5.28 g), N-benzylmethylamine (4.84 g) and 4-toluenesulphonic acid (0.15 g) in toluene (120 ml) was heated under reflux in a Dean and Stark apparatus for 1½ hours by which time all the water produced (approximately 0.8 ml) had been collected by azeotroping. The solvent was then evaporated in vacuo and the residue dissolved in ethanol (150 ml) to which was added sodium borohydride (1.6 g) and the mixture was stirred at room temperature for 17 hours. The solvent was then evaporated in vacuo and the residue carefully diluted with 2M hydrochloric acid (200 ml). The acid solution was extracted twice with methylene chloride (2×100 ml) and the combined organic extracts were evaporated in vacuo to give a residue which was triturated with isopropanol and the resulting precipitate filtered off and dried to afford the title compound, yield 2.5 g, m.p. 204°–206°.

Analysis %: Found: C,74.1; H,7.4; N,5.0; Calculated for $C_{17}H_{19}N.HCl$: C,74.6; H,7.4; N,5.1.

'H-N.m.r. ($CDCl_3$): δ=7.7 (dd, 2H); 7.5 (m, 3H); 7.15 (q, 4H); 4.4 (q, 1H); 4.15 (q, 1H); 4.05 (quintet, 1H); 3.8 (q, 1H); 3.6 (q, 1H); 3.5 (q, 1H); 3.25 (q, 1H); 2.6 (d, 3H).

PREPARATION 11 (ALTERNATIVE TO PREPARATION 10)

2-(N-Benzyl-N-methylamino)indane hydrochloride

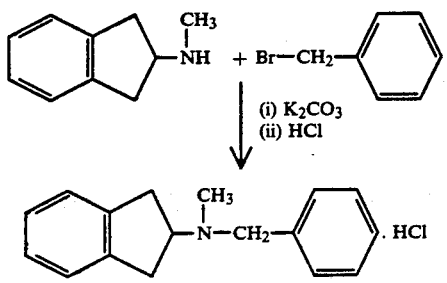

2-Methylaminoindane (0.65 g) (see J. Med. Chem., 1980, 23, page 745), benzyl bromide (0.6 g) and potassium carbonate (1.0 g) were heated under reflux in acetonitrile for 8 hours. The reaction mixture was then filtered and evaporated to dryness in vacuo. The resulting oil was dissolved in ethyl acetate, diluted with ethereal hydrogen chloride and the precipitate collected by filtration and recrystallised from isopropanol to give the title compound, yield 0.5 g, m.p. 204°–206°.

PREPARATION 12

2-[N-Methyl-N-(4-nitrobenzyl)amino]-5-nitroindane

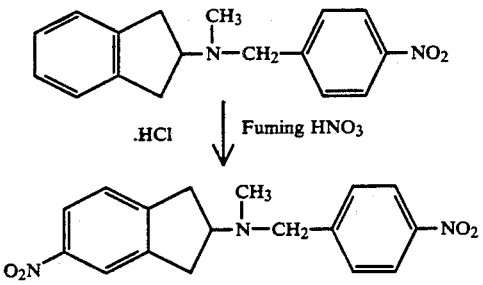

2-[N-Benzyl-N-methylamino]indane hydrochloride (2.6 g) was added portionwise over 10 minutes to fuming nitric acid (25 ml) cooled to −5°. Stirring was continued for a further 2 minutes before the reaction mixture was poured into ice/water. The water was decanted off to leave a gum which was taken up in methylene chloride, washed with water and saturated aqueous sodium bicarbonate, dried ($MgSO_4$) and evaporated in vacuo to give the title compound, yield 2.4 g. A sample (0.1 g) was dissolved in ether and treated with ethereal hydrogen chloride. The resulting precipitate was collected by filtration and dried to give the hydrochloride salt of the title compound, m.p. 210°–212°.

Analysis %: Found: C,55.2; H,5.0; N,11.2; Calculated for $C_{17}H_{17}N_3O_4.HCl. \frac{1}{2}H_2O$: C,54.8; H,5.1; N,11.3 .

'H-N.m.r. (TFAd): δ=8.8 (s, 1H); 8.7 (t, 1H); 8.35 (d, 2H); 8.1 (d, 1H); 7.9 (m, 1H); 7.6 (d, 1H); 5.0 (d, 1H); 4.7 (m, 1H); 4.6 (d, 1H); 3.8 (m, 4H); 3.0 (s, 3H).

PREPARATION 13

5-Amino-2-[N-(4-aminobenzyl)-N-methylamino]indane

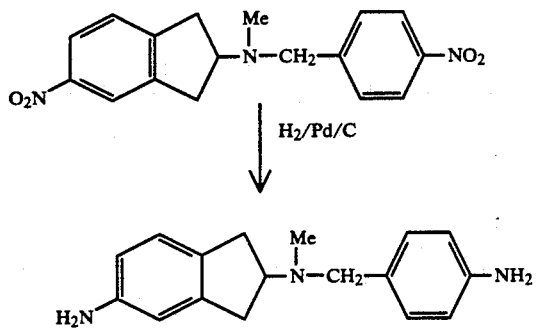

2-[N-Methyl-N-(4-nitrobenzyl)amino]-5-nitroindane (2.3 g) in ethyl acetate (60 ml) containing 5% Pd/C (0.25 g) was stirred under a hydrogen atmosphere [206.8 kPa (30 psi)] for 1 hour at room temperature. The catalyst was then removed by filtration and the filtrate was evaporated to dryness in vacuo. The residue was purified by column chromatography on silica eluting with methylene chloride containing methanol (0% up to 1%). The product-containing fractions were combined and evaporated to give the title compound (1.1 g) as an oil which was used directly without further purification.

We claim:

1. An organic amine compound of the formula:

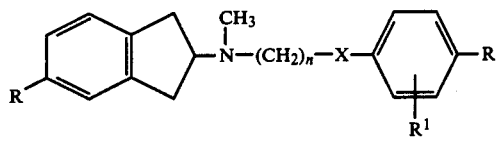

or a pharmaceutically acceptable salt thereof, wherein R, which is the same in each ring, is —$NHSO_2$(-$C_1$–$C_4$ alkyl);

$R^1$ is hydrogen, halogen, $C_1$–$C_4$ alkyl or $C_1$–$C_4$ alkoxy; X is oxygen or a direct link; and n is one or two; with the proviso that when X is oxygen, n is always two.

2. A compound as claimed in claim 1 wherein R is —$NHSO_2CH_3$, $R^1$ is hydrogen and X is oxygen.

3. A compound as claimed in claim 1 wherein R is —$NHSO_2CH_3$, $R^1$ is hydrogen and X is a direct link.

4. A compound as claimed in claim 3 wherein n is one.

5. A compound as claimed in claim 3 wherein n is two.

6. 5-Methanesulphonamido-2-[N-(4-methanesulphonamidophenethyl)-N-methylamino]indane.

7. 5-Methanesulphonamido-2-[N-2{4-methanesulphonamidophenoxy}ethyl)-N-methylamino]indane.

8. A pharmaceutical composition comprising a pharmaceutically acceptable carrier or diluent and an effective anti-arrhythmic amount of a compound as claimed in claim 1.

9. A method for preventing or reducing cardiac arrhythmias in the treatment of a subject afflicted with an impaired cardiac pump function, which comprises administering to said subject an effective anti-arrhythmic amount of a compound as claimed in claim 1.

* * * * *